US010631734B1

(12) United States Patent
Cho et al.

(10) Patent No.: US 10,631,734 B1
(45) Date of Patent: Apr. 28, 2020

(54) METHOD AND SYSTEM FOR MONITORING TISSUE TEMPERATURE

(71) Applicant: ENDRA Life Sciences Inc., Ann Arbor, MI (US)

(72) Inventors: Jang Hwan Cho, Ann Arbor, MI (US); Paul A. Picot, London (CA); Michael M. Thornton, London (CA)

(73) Assignee: ENDRA Life Sciences Inc., Ann Arbor, MI (US)

( * ) Notice: Subject to any disclaimer, the term of this patent is extended or adjusted under 35 U.S.C. 154(b) by 0 days.

(21) Appl. No.: 16/233,959

(22) Filed: Dec. 27, 2018

(51) Int. Cl.
*A61B 5/05* (2006.01)
*A61B 5/00* (2006.01)
*A61B 5/01* (2006.01)
*A61B 5/20* (2006.01)

(52) U.S. Cl.
CPC ............ *A61B 5/0093* (2013.01); *A61B 5/015* (2013.01); *A61B 5/201* (2013.01); *A61B 5/4244* (2013.01); *A61B 5/4519* (2013.01); *A61B 5/489* (2013.01); *A61B 5/4836* (2013.01); *A61B 5/4872* (2013.01); *A61B 5/7278* (2013.01); *A61B 2576/00* (2013.01)

(58) Field of Classification Search
None
See application file for complete search history.

(56) References Cited

U.S. PATENT DOCUMENTS

| 4,385,634 | A | 5/1983 | Bowen |
| 5,713,356 | A | 2/1998 | Kruger |
| 9,706,977 | B2 | 7/2017 | Manohar et al. |
| 2012/0197117 | A1 | 8/2012 | Picot et al. |
| 2017/0348049 | A1* | 12/2017 | Vrba ................... A61B 18/1492 |
| 2017/0351836 | A1* | 12/2017 | Thornton ............. A61B 8/4488 |

OTHER PUBLICATIONS

X. Wang et al., "Microwave-induced thermoacoustic imaging model for potential breast cancer detection," IEEE Trans. Biomed. Eng., vol. 59, No. 10, pp. 2782-2791, Oct. 2012.

(Continued)

*Primary Examiner* — Joel F Brutus
(74) *Attorney, Agent, or Firm* — Stanley E. Jelic (57) ABSTRACT

A system and method utilizing thermoacoustic imaging to estimating tissue temperature within a region of interest that includes an object of interest and a reference which are separated by at least one boundary located at least at two boundary locations. The system and method use a thermoacoustic imaging system that includes an adjustable radio frequency (RF) applicator configured to emit RF energy pulses into the tissue region of interest and heat tissue therein and an acoustic receiver configured to receive bipolar acoustic signals generated in response to heating of tissue in the region of interest; and one or more processors that are able to: process received bipolar acoustic generated in the region of interest in response to the RF energy pulses to determine a peak-to-peak amplitude thereof; and calculate a temperature at the at least two boundary locations using the peak-to-peak amplitudes of the bipolar acoustic signals and a distance between the boundary locations.

15 Claims, 8 Drawing Sheets

(56) References Cited

OTHER PUBLICATIONS

G. Ku and L. V. Wang, "Scanning thermoacoustic tomography in biological tissue," Med. Phys., vol. 27, No. 5, pp. 1195-202, May 2000.
X. L. Dean-Ben, "On the link between the speckle free nature of optoacoustics and visibility of structures in limited-view tomography," Photoacoustics, vol. 4, No. 4, pp. 133-140, Jul. 2016.
C. Gabriel et al., "The dielectric properties of biological tissues: I. Literature survey," Med. Phys., vol. 41, No. 11, pp. 2231-2249, Nov. 1996.
S. Gabriel et al., "The dielectric properties of biological tissues: II. Measurements in the frequency range 10 Hz to 20 GHz," Med. Phys., vol. 41, No. 11, pp. 2251-2269, Nov. 1996.
M. Pramanik et al., "Thermoacoustic and photoacoustic sensing of temperature," J. of Biomedical Optics, vol. 14, No. 5, Sep. 2009.
C. Lou et al., "Temperature monitoring utilising thermoacoustic signals during pulsed microwave thermotherapy: A feasibility study," Int. J. Hyperthermia, vol. 26, No. 4, pp. 338-346, 2010.

\* cited by examiner

METHOD AND SYSTEM FOR MONITORING TISSUE TEMPERATURE

FIELD

The subject disclosure relates to thermoacoustic imaging and in particular, to a method and system for monitoring tissue temperature.

BACKGROUND

During thermotherapy or cryotherapy, it is necessary to, monitor temperature distribution in the tissues to ensure safe deposition of heat energy in the surrounding healthy tissue and for efficient destruction of tumor and abnormal cells. To this end, real-time temperature monitoring with spatial resolution (approximately 1 millimeter) and high temperature sensitivity (1 degree Kelvin or better) is needed.

The most accurate temperature monitoring is by directly measuring the temperature with a thermocouple or thermistor. However, directly measuring the temperature is invasive, is generally not preferred, and is simply not feasible.

Several non-invasive temperature monitoring methods have been developed. For example, infrared thermography has been, used to monitor tissue temperature. Although infrared thermography has 0.1 degree Celsius accuracy, it is limited to only superficial temperatures.

Ultrasound has been used to monitor tissue temperature. Although ultrasound has good spatial resolution and high penetration depth, the temperature sensitivity of ultrasound is low.

Magnetic resonance imaging has been used to monitor tissue temperature. Although magnetic resonance imaging has advantages of high resolution and sensitivity, magnetic resonance imaging is expensive, bulky, and slow.

Although techniques for monitoring tissue temperature have been considered, improvements are desired. It is therefore an object at least to provide a novel method and system for monitoring tissue temperature.

SUMMARY

It should be appreciated that this Summary is provided to introduce a selection of concepts in a simplified form that are further described below in the Detailed Description. This Summary is not intended to be used to limit the scope of the claimed subject matter.

Accordingly, in one aspect there is provided a method for estimating tissue temperature, the method comprising (i) directing, using a radio frequency (RF) applicator, one or more RF energy pulses into the tissue region of interest, the tissue region of interest comprising an object of interest and at least one reference that are separated by at least one boundary at least at two boundary locations; (ii) detecting, using an acoustic receiver, bipolar acoustic signals generated in the region of interest at each boundary location in response to the RF energy pulses and processing the bipolar acoustic signals to determine peak-to-peak amplitudes thereof; and (iii) calculating a temperature at the at least two boundary locations using the peak-to-peak amplitudes of the bipolar acoustic signals and a distance, between the boundary locations.

In one or more embodiments, the method comprises calculating the distance between the boundary locations.

In one or more embodiments, the distance between the boundary locations is an effective distance between the boundary locations.

In one or more embodiments, the method comprises estimating a temperature of the object of interest based on the calculated temperature at the at least two boundary locations.

In one or more embodiments, the method comprises detecting, using the acoustic receiver, at least one other bipolar acoustic signal generated by a second object of interest in response to the RE energy pulses and processing the at least one other bipolar acoustic signal to determine a peak-to-peak amplitude thereof.

In one or more embodiments, the method comprises comprising comparing the peak-to-peak amplitude of the bipolar acoustic signal, the calculated temperature at the at least two boundary locations and the peak-to-peak amplitude of the other bipolar acoustic signal to estimate a temperature of the second object of interest.

In one or more embodiments, the boundary is at a location between at least two different types of tissue.

In one or more embodiments, the two different types of tissue are one of muscle and fat; a blood vessel and fat; and liver tissue and kidney tissue.

In one or more embodiments, the method comprises repeating steps (i) to (iii) during treatment to continuously monitor tissue temperature.

According to another aspect there is provided a system for determining tissue temperature within a region of interest comprising an object of interest and a reference that are separated by at least one boundary at least at two boundary locations, the system comprising a thermoacoustic imaging system comprising an adjustable radio frequency (RF) applicator configured to emit RF energy pulses into the tissue region of interest and heat tissue therein and an acoustic receiver configured to receive bipolar acoustic signals, generated in response to heating of tissue in the region of interest; and one or more processors configured to process received bipolar acoustic generated in the region of interest in response to the RE energy pulses to determine a peak-to-peak amplitude thereof; and calculating a temperature at the at least two boundary locations using the peak-to-peak amplitudes of the bipolar acoustic signals and a distance between the boundary locations.

In one or more embodiments, the one or more processors are further configured to calculate the distance between the boundary locations.

In one or more embodiments, the distance between the boundary locations is an effective distance between the boundary locations.

In one or more embodiments, the one or more processors are further configured to estimate a temperature of the object of interest based on the calculated temperature at the at least two boundary locations.

In one or more embodiments, the one or more processors are further configured to detect, using the acoustic receiver, at least one other bipolar acoustic signal generated by a second object of interest in response to the RF energy pulses and process the at least one other bipolar acoustic signal to determine a peak-to-peak amplitude thereof.

In one or more embodiments, the one or more processors are further configured to compare the peak-to-peak amplitude of the bipolar acoustic signal, the calculated temperature at the at least two boundary locations and the peak-to-peak amplitude of the other bipolar acoustic signal to estimate a temperature of the second object of interest.

According to another aspect there is provided a method of monitoring tissue temperature, the method comprising (i) directing, using a radio frequency (RF) applicator, one or more RF energy pulses into the tissue region of interest, the tissue region of interest comprising an object of interest and at least one reference that are separated by at least one boundary at least at two boundary locations; (ii) detecting, using an acoustic receiver, bipolar acoustic signals generated in the region of interest at, each boundary location in response to the RF energy pulses and, processing the bipolar acoustic signals\ to determine peak-to-peak amplitudes thereof; (iii) calculating a temperature at the at least two boundary locations using the peak-to-peak amplitudes of the bipolar acoustic signals and a distance between the boundary locations; and (iv) repeating the directing, detecting and calculating to monitor the temperature at the at least one boundary.

BRIEF DESCRIPTION OF THE DRAWINGS

Embodiments will now be described more fully with reference to the accompanying drawings in which.

DETAILED DESCRIPTION OF THE EMBODIMENTS

The foregoing summary, as well as the following, detailed description of certain examples will be better understood when read in conjunction with the appended drawings. As used herein, an element or feature introduced in the singular and preceded by the word "a" or "an" should be understood as not necessarily excluding the plural of the elements or features. Further, references to "one example" or "one embodiment" are not intended to be interpreted as excluding the existence of additional examples or embodiments that also incorporate the described elements or features. Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including but not limited to" and the terms "comprising", "having" and "including" have equivalent meanings.

As used herein, the term "and/or" can include any and all combinations of one or more of the associated listed elements or features.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "back" and the like, may be used herein for ease of description to describe the relationship of an element or feature to another element or feature as illustrated in the figures. The spatially relative terms can however, encompass different orientations in use or operation in addition to the orientations depicted in the figures.

In the following, a method and system for estimating tissue temperature are described. Generally, the method and system utilize, an RF applicator to obtain thermoacoustic data of tissue within a region of interest (ROI) of a subject. The thermoacoustic data is analyzed to estimate tissue temperature.

Figure 1:
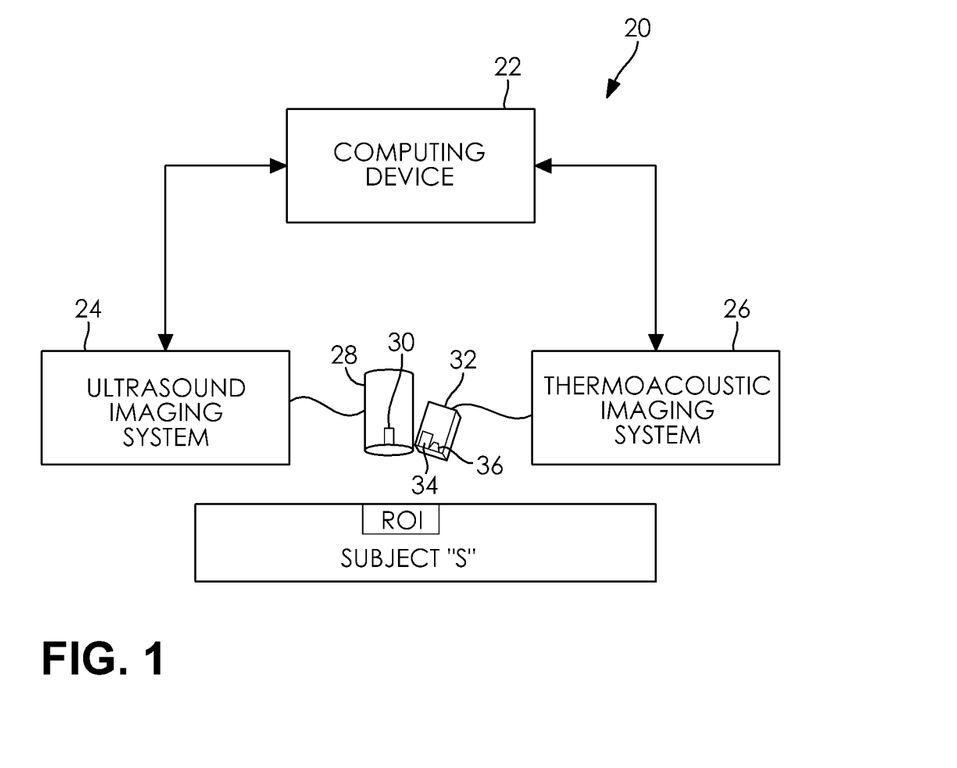
FIG. 1 is a schematic view of an imaging system.

Turning now to FIG. 1, an exemplary imaging system is shown and is generally identified by reference numeral 20. As can be seen, the imaging system 20 comprises a programmed computing device 22 communicatively coupled to an ultrasound imaging system 24 and to a thermoacoustic imaging system 26. The ultrasound imaging system 24 and thermoacoustic imaging system 26 are configured to obtain ultrasound image data and thermoacoustic image data, respectively, of a tissue region of interest ROI associated with a subject S.

The programmed computing device 22 in this embodiment is a personal computer or other suitable processing device comprising, for example, a processing unit comprising one or more processors, system memory (volatile and/or non-volatile memory), other non-removable or removable memory (e.g., a hard disk drive, RAM, ROM, EEPROM, CD-ROM, DVD, flash memory, etc.) and a system bus coupling the various computer components to the processing unit. The computing device 22 may also comprise networking capabilities using Ethernet, Wi-Fi, and/or other suitable network format, to enable connection to shared or remote drives, one or more networked computers, or other networked devices. One or more input devices, such as a mouse and a keyboard (not shown) are coupled to the computing device 22 for receiving operator input. A display device (not shown), such as one or more computer screens or monitors, is coupled to the computing device 22 for displaying one or more generated images that are based on ultrasound image data received from the ultrasound imaging system 24 and/or the thermoacoustic image data received from thermoacoustic imaging system 26.

The ultrasound imaging system 24 comprises an acoustic receiver in the form of an ultrasound transducer 28 that houses one or more ultrasound transducer arrays 30 configured to emit sound waves into the region of interest ROI of the subject S. The sound waves directed into the region of interest ROI of the subject echo off tissue within the region of interest ROI, with different tissues reflecting varying degrees of sound. Echoes that are received by the one or more ultrasound transducer arrays 30 are processed by the ultrasound imaging system 24 before being communicated as ultrasound image data to the computing device 22 for further processing and for presentation as ultrasound images that can be interpreted by an operator. In this embodiment, the ultrasound imaging system 24 utilizes B-mode ultrasound imaging techniques assuming a nominal speed of sound of 1,540 m/s. As ultrasound imaging systems are known in the art, further specifics of the ultrasound imaging system 24 will not be described, further herein.

The thermoacoustic imaging system 26 comprises an acoustic receiver in the form of a thermoacoustic transducer 32. The thermoacoustic transducer 32 houses one or more thermoacoustic transducer arrays 34 as well as a radio frequency (RF) applicator 36. It will however be appreciated that the RF applicator 36 may be housed separately from the thermoacoustic transducer 32. The RF applicator 36 is configured to emit short pulses of RF energy that are directed into tissue within the region of interest ROI of the subject. In this embodiment, the RF applicator 36 has a frequency between about 10 Mhz and 100 GHz and has a pulse duration between about 0.1 nanoseconds and 10 nanoseconds. The RF energy pulses delivered to the tissue within the region of interest ROI heat the tissue thereby to induce acoustic pressure waves that are detected by the thermoacoustic transducer 32. The acoustic pressure waves that are detected by the thermoacoustic transducer 32 are processed and communicated as thermoacoustic image data to the computing device 22 for further processing and for presentation as thermoacoustic images that can be interpreted by the operator.

In this embodiment, the ultrasound transducer 28 and thermoacoustic transducer 32 are mechanically interconnected so that the spatial relationship between the one or more ultrasound transducer arrays 30, the one or more thermoacoustic arrays 34 and the RF applicator 36 are known. The spatial relationship is set using a centerline of the one or more ultrasound transducer arrays 34, the one or more thermoacoustic transducer arrays 34, and RF applicator 36. Each centerline is defined as being a mid-point of an area of the respective transduce array.

In this embodiment, the spatial relationship between the one or more ultrasound transducer arrays 30 and the one or more thermoacoustic transducer arrays 34 is such that the centerline of the one or more thermoacoustic transducer arrays 34 is set at know angle α with respect to the centerline (also known as the axial axis or ultrasound transducer array beam axis) of the one or more ultrasound transducer arrays 30. The spatial relationship between the one or more thermoacoustic transducer arrays 34 and the RF applicator 36 is such that the centerline of the RF applicator 36 is spaced-apart and generally parallel to the centerline of the one or more thermoacoustic transducer arrays 34.

The imaging system 20 utilizes the known spatial relationship between the one or more ultrasound transducer arrays 30 and the one or more thermoacoustic transducer arrays 34 to increase the precision and accuracy of thermoacoustic imaging.

The coordinate system of the one or more ultrasound transducer arrays 30 of the ultrasound transducer 28 and the coordinate system of the one or more thermoacoustic transducer arrays 34 of the thermoacoustic transducer 32 are mapped by the computing device 22 so that acquired ultrasound and thermoacoustic images can be registered. Alternatively, the thermoacoustic imaging system 26 may make use of the one or more ultrasound transducer arrays 30 of the ultrasound transducer 28 by disconnecting the one or more ultrasound transducer arrays 30 from the ultrasound transducer 28 and connecting the one or more ultrasound transducer arrays 30 to the thermoacoustic transducer 32. As will be appreciated, by doing this coordinate mapping between the one or more ultrasound transducer arrays 28 and the one or more thermoacoustic transducer arrays 34 is not required.

During thermoacoustic imaging of a region of interest that includes a boundary between fat or fatty tissue and soft or lean tissue, bipolar acoustic signals are generated that are received by the thermoacoustic transducer 32. This is due to the fact that the soft or lean tissue absorbs more heat than the fat or fatty tissue causing it to expand rapidly across the boundary and into the fat or fatty tissue, that expands less, and then quickly contract. The strength or peak-to-peak values of the bipolar acoustic signals depend on the relative absorption properties of the fat or fatty tissue and the soft or lean tissue. The strength or peak-to-peak values of the bipolar acoustic signals also depend on the temperature of the boundary between the fat or fatty tissue and soft or lean tissue.

Figure 2:
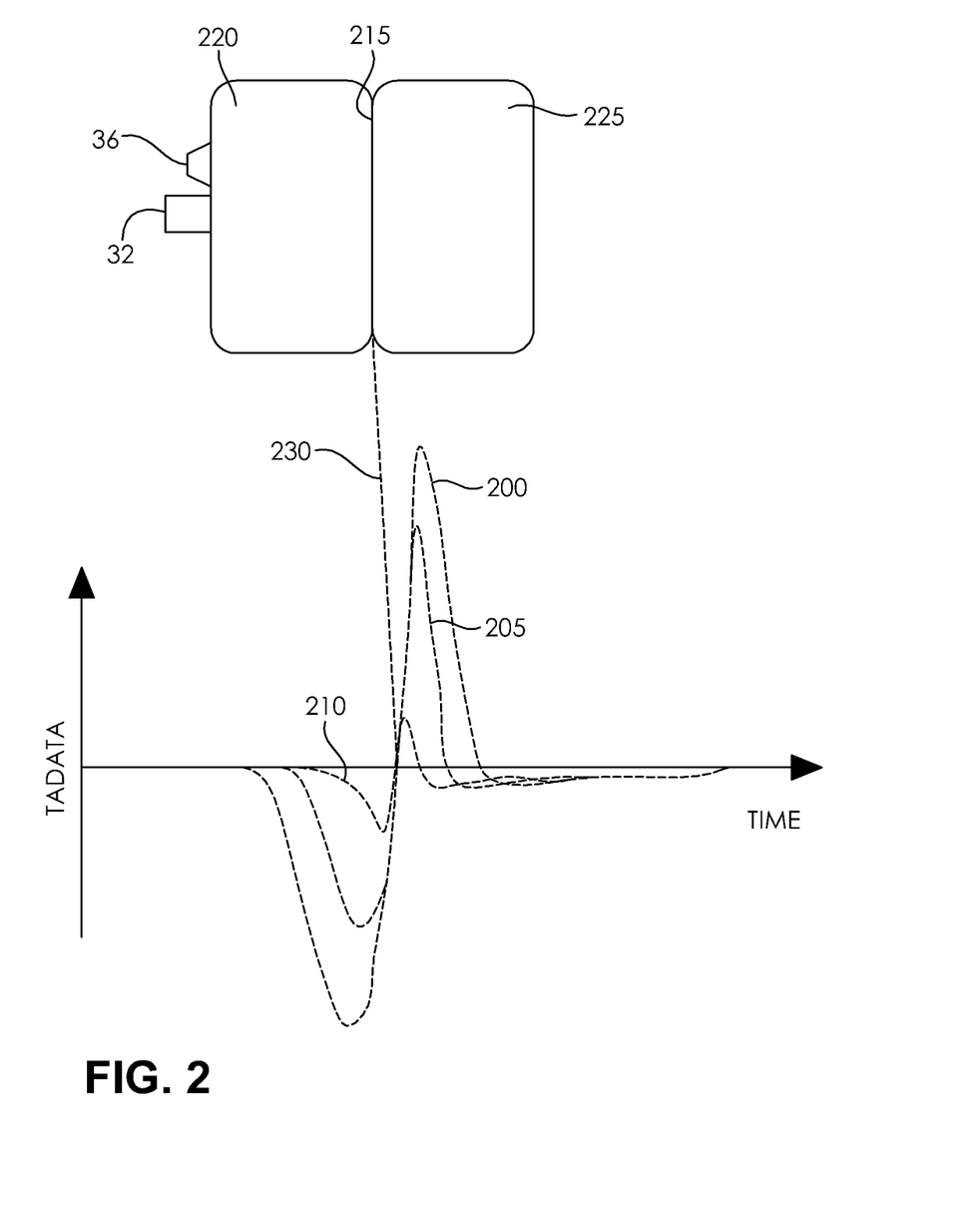
FIG. 2 is a graph showing exemplary bipolar acoustic signals.

Exemplary bipolar acoustic signals 200, 205 and 210 are shown in FIG. 2. The bipolar acoustic signals 200, 205 and 210 are generated in response to thermoacoustic imaging of a tissue region of interest ROI comprising a first tissue 220 and a different type of second tissue 225 that are separated by a boundary 215. The dashed line 230 indicates a time point corresponding to the boundary 215. The differences in the peak-to-peak values of the bipolar acoustic signals 200, 205 and 210 represent the extent to which the first tissue 220 expands into the boundary 215 and into the second tissue 225 before contracting. As the temperature of the boundary 215 increases, the amount that the first tissue 220 expands into the boundary 215 and into the second tissue 225 increases. As such, the peak-to-peak amplitude of each bipolar acoustic signal 200, 205 and 210 is proportional to a temperature at the boundary 215. As can be seen, the peak-to-peak value of bipolar acoustic signal 200 is greater than that of bipolar acoustic signals 205, 210 and the peak-to-peak value of bipolar acoustic signal 205 is greater than that of bipolar acoustic signal 210. As such, the temperature of the boundary 215 when bipolar acoustic signal 200 is generated is greater than the temperature of the boundary 215 when bipolar signal 205 is generated. Similarly, the temperature of the boundary 215 when bipolar acoustic signal 205 is generated is greater than the temperature of the boundary 215 when bipolar signal 210 is generated.

Figure 3:
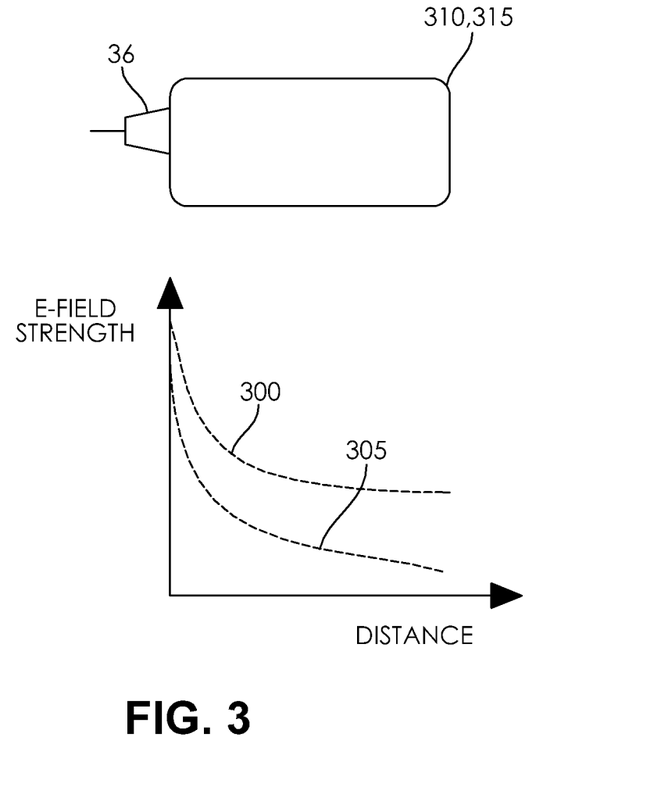
FIG. 3 is a graph showing exemplary electric field strength attenuation curves.

Exemplary electric field strength attenuation curves 300 and 305 are shown in FIG. 3. Each electric field strength attenuation curve 300, 305 represents the electric field strength attenuation of tissue 310, 315, respectively, as a function of distance from the RF applicator 36 of the thermoacoustic imaging system 26. The tissue 310 associated with electric field strength attenuation curve 300 has a different temperature and Grüneisen parameter than the tissue 315 associated with electric field strength attenuation curve 305. As will be appreciated, temperature has either a positive or negative effect on thermoacoustic bipolar signals depending on the temperature relationship between electric field strength and Grüneisen parameter for a respective type of tissue.

The imaging system 20 exploits the relationship between thermoacoustic bipolar signals and temperature to estimate tissue temperature during thermoacoustic imaging.

Figure 4:
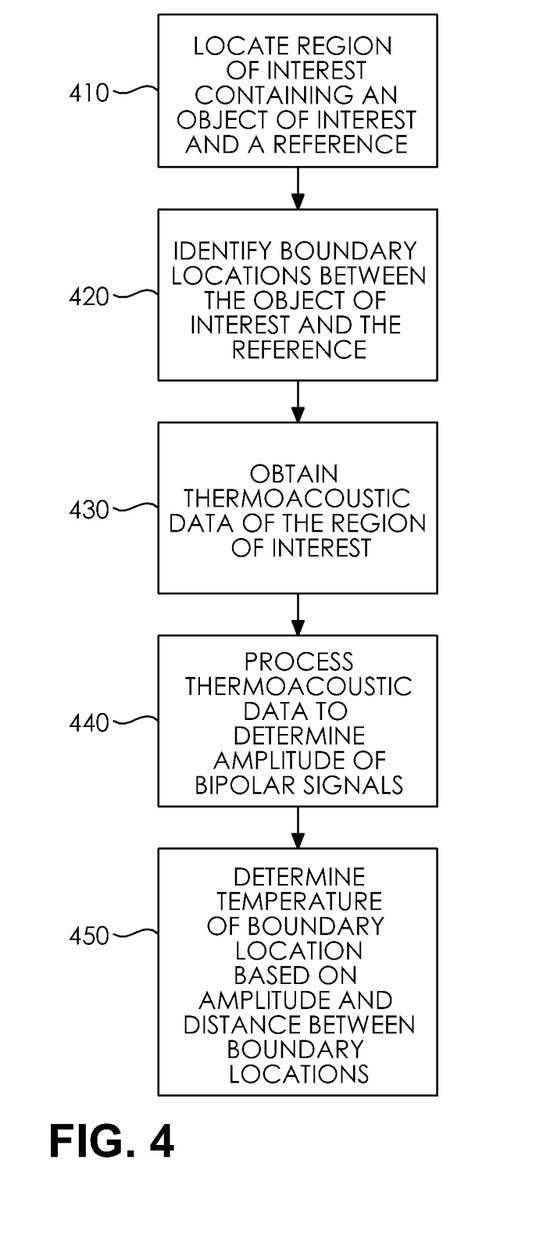
FIG. 4 is a flowchart of a method for estimating tissue temperature.

Turning now to FIG. 4, a method of determining tissue temperature during thermoacoustic imaging is shown. Initially during the method, a region of interest ROI within the subject S to be imaged that contains an object of interest and a reference separated by at least one boundary at least at two locations is located (step 410). In this embodiment, the region of interest ROI is located using the ultrasound imaging system 24. Specifically, ultrasound image data obtained by the ultrasound imaging system 24 is communicated to the computing device 22. The ultrasound image data is processed by the computing device 22 and a reconstructed ultrasound image is presented on the display device. The operator moves the ultrasound transducer 28 on the subject's body until the region of interest is located. When locating the region of interest, the computing device 22 overlays information associated with the angle of the centerline of the one or more transducer arrays 30 of the ultrasound transducer 28 overtop of the reconstructed ultrasound image on the display device. The information is used to provide feedback to the operator to ensure the axial axis of the ultrasound transducer 28 is generally perpendicular to a boundary between the object of interest and the reference.

Figure 5:
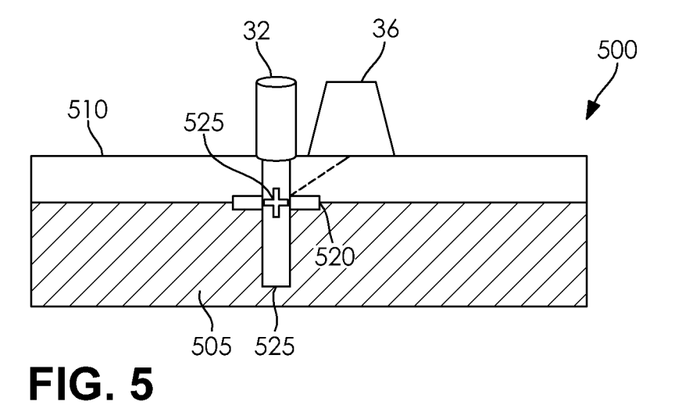
FIG. 5 is an exemplary region of interest containing an object of interest and a reference.

An exemplary region of interest 500 containing an object of interest 505 and a reference 510 is shown in FIG. 5. In this embodiment, the object of interest 505 is the subject's liver and the reference 510 is the subject's kidney. Also shown in FIG. 5 is the RF applicator 36 and the thermoacoustic transducer 32.

Boundary locations between the object of interest and the reference are identified in the reconstructed ultrasound image (step 420). In this embodiment, two boundary locations are identified. Each boundary location is identified by the operator using an input device such as a mouse coupled to the computing device 22. Specifically, the operator draws a box that encompasses at least, a portion of the object of interest 505, at least a portion of the reference 510 and, the identified boundary between the portions of the object of interest and the reference. The computing device 22 provides feedback to the operator via the display device to indicate the approximate angle between the box and the boundary to ensure the box is generally perpendicular to the boundary.

An exemplary box 515 is shown in FIG. 5. As can be seen, the box 515 encompasses a portion of the object of interest 505 (the liver), a portion of the reference 510 (the kidney), and the boundary 520 between the object of interest 505 and the reference 510. The boundary 520 is selected at a particular boundary location 525 where the liver and the kidney are in close relation to one another.

The RF applicator 36 is conditioned to generate short RF energy pulses. The RF energy pulses are directed into the region of interest 500 to deliver energy to the object of interest 505 and the reference 510 within the region of interest ROI. At each boundary location, bipolar acoustic signals are generated that are detected by the thermoacoustic transducer 32 (step 430).

Since the angle α between the centerline of the one or more transducer arrays 30 of the ultrasound transducer 28 and the centerline of the one or more transducer arrays 34 of the thermoacoustic transducer 32 is known, the operator is able to adjust position of the thermoacoustic transducer 32 with respect to the subject's body such that the thermoacoustic imaging system 26 is able to obtain thermoacoustic image data of the region of interest at a desired imaging angle σ. The desired imaging angle σ is such that the centerline of the one or more transducer arrays 34 of the thermoacoustic transducer 32 extends through the boundary 520 between the object of interest 505 and the reference 510.

The bipolar acoustic signals are in turn communicated to the computing device 22 for processing (step 440). In this embodiment, the computing device 22 is programmed to determine the peak-to-peak amplitudes of the bipolar acoustic signals.

The temperature at each boundary location is determined using the peak-to-peak amplitudes of the bipolar acoustic signals (step 450). In this embodiment, the temperature at each boundary location is determined based on the following.

The pressure rise of the acoustic pressure wave is proportional to a dimensionless parameter called a Grüneisen parameter and local fluence. The local fluence is dependent on tissue parameters such as for example the absorption coefficient, scattering coefficient and anisotropy factor. The local fluence does not change significantly with temperature.

Figure 8:
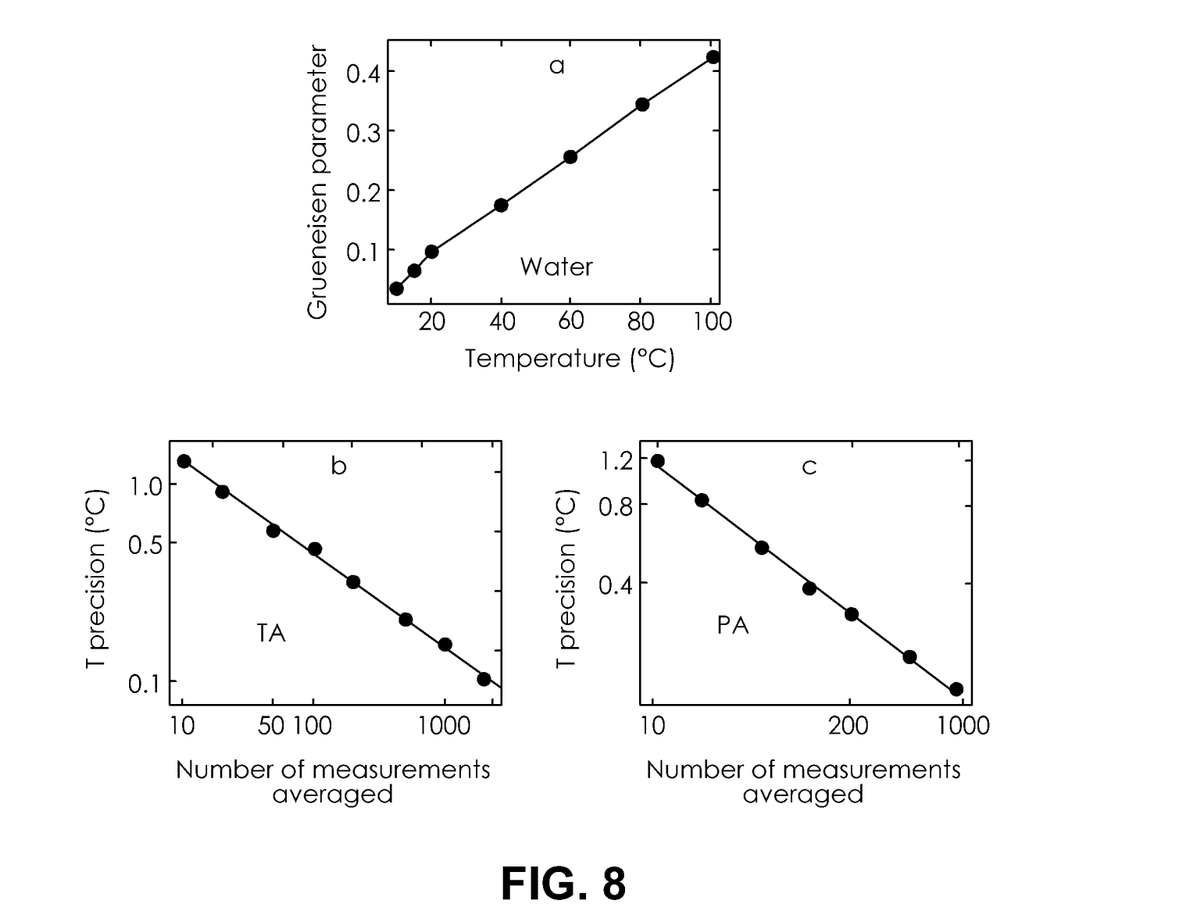
FIG. 8 is a graph showing how the Grüneisen parameter changes with temperature.

The Grüneisen parameter is dependent on isothermal compressibility, the thermal coefficient of volume expansion, the mass density, and the specific heat capacity at constant volume of the tissue. As shown in FIG. 8, the Grüneisen parameter changes significantly with temperature. As such, the strength or peak-to-peak value of the bipolar acoustic signal generated from the acoustic pressure wave is dependent on tissue temperature.

Using the Grüneisen parameter and strength or peak-to-peak value of the bipolar acoustic signal, the temperature of the boundary can be determined. In this embodiment, the temperature of the boundary is calculated using the following equations.

The thermoacoustic pressure p($\underline{r}$, t) produced by a heat source H($\underline{r}$, t) obeys the following equation:

$$\nabla^2 p(\underline{r}, t) - \frac{1}{c^2} \frac{\partial^2}{\partial t^2} p(\underline{r}, t) = -\frac{\beta}{C_p} \frac{\partial}{\partial t} H(\underline{r}, t) \qquad (1)$$

where $\underline{r}$ is the spatial position vector, β is the isobaric volume expansion coefficient, c is the sound speed and $C_p$ is the specific heat capacity. Solving equation 1 with respect to the acoustic pressure wave p($\underline{r}$, t) yields the following forward, problem:

$$p(\underline{r}, t) = \frac{\beta}{4\pi C_p} \int \int \int \frac{\partial r}{|\underline{r} - \underline{r}'|} \frac{\partial H(\underline{r}', t')}{\partial t'} \bigg|_{t' = t - \frac{r'}{c}} \qquad (2)$$

The heat source H($\underline{r}$, t) is modeled as the product of two factors which are the spatial distribution of energy absorption A($\underline{r}$) and the temporal irradiation function I(t). The spatial distribution of energy absorption A($\underline{r}$) is determined based on characteristics of the tissue(s) being imaged. Since the thermoacoustic transducer array 30 has a finite bandwidth, received thermoacoustic data $p_d$($\underline{r}$, t) is a result of the convolution of acoustic pressure wave p($\underline{r}$, t) and the impulse response of the thermoacoustic transducer array 30 h(t) as set out in equation 3:

$$p_d(\underline{r},t) = p(\underline{r},t) *_t h(t) \qquad (3)$$

where $*_t$ denotes a one-dimensional temporal convolution.

As will be appreciated, for conventional thermoacoustic imaging, the goal is to recover the spatial absorption distribution A(r) by inverting the forward problem. As such, the irradiation function is modeled as a temporal function that is uniform throughout the field at a given time point.

Due to the limited bandwidth of the thermoacoustic transducer array used to receive thermoacoustic data, accurately recovering the absorption distribution is not trivial. As such, extracting quantitative information such as tissue temperature from thermoacoustic data requires sophisticated methods beyond that of conventional reconstruction methods.

When the region of interest is heated with a pulse of RF energy, the power deposition per unit volume A($\underline{r}$) is expressed as:

$$A(\underline{r}) = \omega \varepsilon_0 \varepsilon_r'' E^2(\underline{r}) \qquad (4)$$

where ω is the radian frequency, $\varepsilon_0$ is the vacuum permittivity, $\varepsilon_r''$ is the imaginary part of the relative permittivity of the tissue and E(r) is the electric field strength. The strength of thermoacoustic data S(r) obtained from a tissue is the product of the deposited energy and the Grüneisen parameter of the tissue Γ:

$$S(\underline{r})=\Gamma A(\underline{r})=\Gamma \omega \varepsilon_0 \varepsilon_r'' E^2(\underline{r}) \quad (5)$$

Within dielectric lossy medium, the electric field strength is attenuated as it propagates through the medium. The amount of attenuation is determined by various factors such as for example characteristics of region of interest and characteristics of the RF applicator 36. The spatial distribution of the electric field is:

$$E(\underline{r})=E_0 E_A(\underline{r}) \quad (6)$$

where $E_0$ is the maximum electric field strength forward to the region of interest and $E_A(\underline{r})$ is the attenuation of the electric field over a given space. For a simple 1D case, the attenuation $E_A(\underline{r})$ can be expressed in exponential form:

$$E_A(d)=e^{-\eta d} \quad (7)$$

where η is the electric field absorption coefficient of the region of interest and d is the distance of the region of interest from the applicator.

As mentioned, the strength or peak-to-peak amplitudes of the bipolar signals represent the absorption property difference between the object of interest and the reference. Further, the phase of the thermoacoustic data at the boundary indicates which tissue (object of interest or the reference) has a higher or lower absorption coefficient. The strength or peak-to-peak amplitudes $S_I$ of the thermoacoustic signals measured at the boundary location, $r_I$, is expressed in equation 8.0:

$$S_I=\mu(\Gamma_1\varepsilon_{r,1}''-\Gamma_2\varepsilon_{r,2}'')\omega\varepsilon_0 E_I^2 \quad (8.0)$$

where subscripts 1 and 2 denote two different tissues located on each side of the boundary, $r_I$, and $E_I$ denotes the incident electric field strength at the boundary, and μ is a calibration scaling constant. The calibration scaling constant of the given system will depend on various factors such as transducer characteristics and applied signal processing techniques. Without loss of generality, the value of the calibration scaling constant can assumed to be 1 for the derivations below.

As shown in equation 8.0, the strength of the acquired thermoacoustic data is determined by tissue properties and the strength of the electric field.

The strength or peak-to-peak amplitudes of the bipolar acoustic signals are different at each boundary location due to the attenuation of the electric field between the boundary locations. Since the object of interest is located near the boundary locations, the attenuation of the electric field is characterized by the dielectric properties of the object of interest and this can be used to estimate the temperature of the object of interest.

Using the above equations, the ratio is expressed as:

$$\frac{S_{L,Reference\,A}}{S_{L,Reference\,B}} = \frac{\Gamma_L\varepsilon_{r,L}'' - \Gamma_A\varepsilon_{r,A}'' E_A^2(r_{Location\,1})}{\Gamma_L\varepsilon_{r,L}'' - \Gamma_B\varepsilon_{r,B}'' E_B^2(r_{Location\,2})} \quad (9.0)$$

$$\frac{E_A(r_{Location\,1})}{E_B(r_{Location\,2})} \equiv e^{-\eta_{object\,of\,interest} d_{eff}(r_{Location\,1}, r_{Location\,2})} \quad (10.0)$$

where L denotes the object of interest, A and B denote the boundary locations. As will be appreciated, the ratio is an exponential term defined using the absorption coefficient of the object of interest and the distance between the boundary locations. The effective distance $d_{eff}$ is the distance between the boundary locations ($r_{Location\,1}, r_{Location\,2}$) that contributes to the electric field attenuation. As such, the effective distance between the two boundary locations may be different from the actual physical distance between them. The effective distance $d_{en}$ is determined based on the design of the RF applicator and the expected electric field pattern. For example, the electric field distribution may have a hemispheric shape centered at the RF applicator. In such case, the effective distance between two points on the surface of the same concentric sphere is zero. The difference between the distances from the origin of the hemisphere to each respective boundary location is the effective distance between boundary locations.

The Grüneisen parameter of the tissue Γ is a function of temperature. In this embodiment, it is assumed that the relationship between the Grüneisen parameter of the tissue F and temperature of the tissue is linear:

$$\Gamma(T)=aT+b \quad (8.1)$$

Where a is the slope of the linear relationship, T is an offset of the temperature which applies to a linear portion of the modeled temperature range (for example corresponding to a linear temperature range of 20 to 80 degrees Celsius), and, b is the value at T=0. It will be appreciated that in other embodiments higher order functions or other types of mathematical relationships can be used.

Using the linear relationship of equation 8.1, equation 8.0 is rewritten as:

$$S_I=((a_1T+b_1)\varepsilon_{r,1}''-(a_2T+b_2)\varepsilon_{r,2}'')\omega\varepsilon_0 E_I^2 \quad (8.2)$$

Equation 9.0 can be solved for T:

$$T = \frac{(1-X)b_L\varepsilon_{r,L}'' - b_A\varepsilon_{r,A}'' + Xb_B\varepsilon_{r,B}''}{(X-1)a_L\varepsilon_{r,L}'' + a_A\varepsilon_{r,A}'' - Xa_B\varepsilon_{r,B}''} \quad (9.1)$$

where $$X \equiv \frac{S_A}{S_B} \frac{E_B^2(r_{Location\,2})}{E_A^2(r_{Location\,1})} \quad (9.2)$$

As will be appreciated, the dielectric properties of tissue are also temperature dependent. For each tissue type the relationship between the dielectric properties and temperature are unique. The above equations assume that the dielectric properties of tissue are fixed. To more accurately determine temperature, the permittivity of each tissue type is modeled as a function of temperature. As a result, equation (8.2) is rewritten as:

$$S_I=(\Gamma_1(T)\varepsilon_{r,1}''(T)-\Gamma_2(T)\varepsilon_{r,2}''(T))\omega\varepsilon_0 E_I^2 \quad (8.3)$$

or $$S_I=((a_1T+b_1)\varepsilon_{r,1}''(T)-(a_2T+b_2)\varepsilon_{r,2}''(T))\omega\varepsilon_0 E_I^2 \quad (8.4)$$

By rearranging terms, the following function of temperature is defined:

$$g(T) = \frac{(a_LT+b_L)\varepsilon_{r,L}''(T) - (a_AT+b_A)\varepsilon_{r,A}''(T)}{(a_LT+b_L)\varepsilon_{r,L}''(T) - (a_BT+b_B)\varepsilon_{r,B}''(T)} = \frac{S_A}{S_B} \frac{E_B^2(r_{Location\,2})}{E_A^2(r_{Location\,1})} \quad (11)$$

As such, for different temperatures, the function g(T) is tabulated from models and experiments.

The electric field attenuation of tissue depends on temperature. As such, equation 10.0 can be rewritten as:

$$\frac{E_A(r_{Location\,1})}{E_B(r_{Location\,2})} \equiv e^{-\eta_{object\,of\,interest}(T)d_{eff}(r_{Location\,1},r_{Location\,2})} \quad (10.1)$$

Using equations 10.1 and 11, the following function of temperature is defined:

$$h(T) = \frac{(a_L T + b_L)\varepsilon''_{r,L}(T) - (a_A T + b_A)\varepsilon''_{r,A}(T)}{(a_L T + b_L)\varepsilon''_{r,L}(T) - (a_B T + b_B)\varepsilon''_{r,B}(T)} e^{2\eta_{object\,of\,interest}(T)} = \quad (12)$$

$$\frac{S_A}{S_B} e^{-2d_{eff}(r_{Location\,1},r_{Location\,2})}$$

For different temperatures, the function h(T) may be tabulated from models and experiments. Each component of h(T) is either measured or modeled for different temperatures. Using the function h(T) the temperature at the boundary locations is determined.

It is assumed that the object of interest and reference have the same temperature as the boundary locations. As such, once the temperature at the boundary locations is determined, the temperature of the object of interest and the reference are estimated. Steps 430 to 450 may be repeated to continuously monitor the temperature of the object of interest during medical procedures such as for example during hyperthermia treatment.

Figure 6:
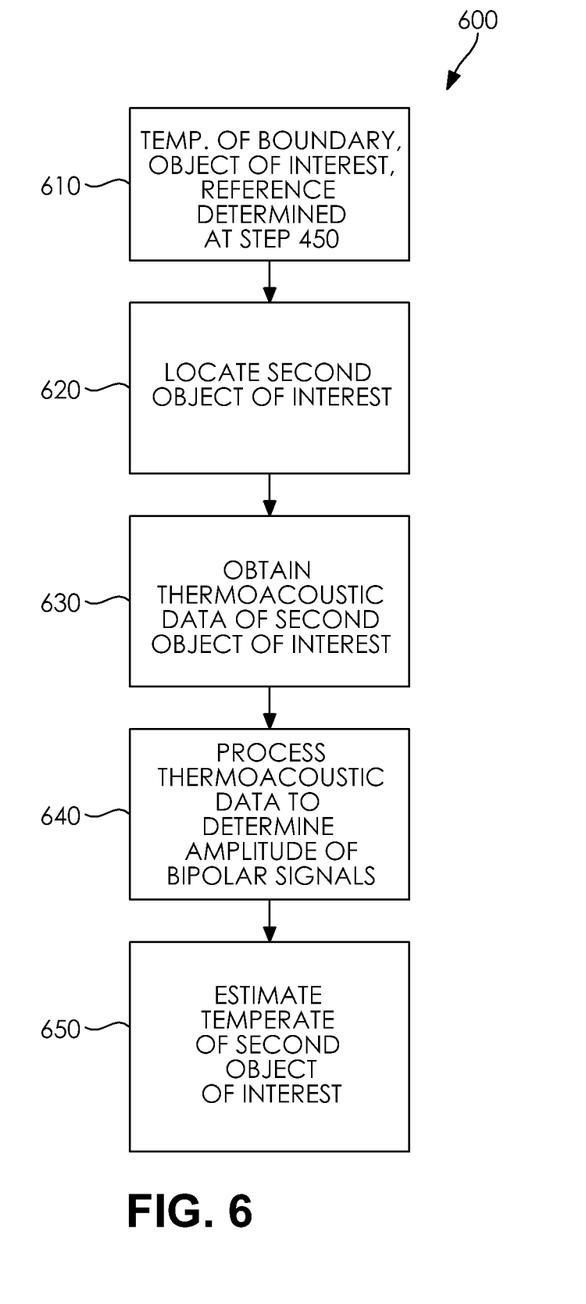
FIG. 6 is a flowchart of another method for estimating tissue temperature.

In another embodiment, the temperature of the boundary, object of interest and reference may be used to estimate the temperature of a second object of interest (which in a separate embodiment, can correspond to the entire region of interest or an area affected by a medical procedure). An exemplary method 600 is shown in FIG. 6. The method follows step 450 described above, wherein the temperature of the boundary locations, object of interest and reference are determined (step 610). A second object of interest is located using the ultrasound imaging system 24 (step 620). In this embodiment, the second object of interest is a tumour. RF energy pulses are directed to deliver energy to the second object of interest. In response, bipolar acoustic signals are generated that are detected by the thermoacoustic transducer 32 (step 630). The bipolar acoustic signals are communicated to the computing device 22 for processing (step 640). In this embodiment, the computing device 22 is programmed to determine the peak-to-peak amplitudes of the bipolar acoustic signals.

By comparing the peak-to-peak amplitudes of the bipolar acoustic signals determined during step 440, the temperature of the boundary locations, object of interest and reference determined during, step 450, and the peak-to-peak amplitudes of the bipolar acoustic signals determined during step 640, the temperature of the second object of interest may be estimated (step 650). Steps 610 to 650 may be repeated to continuously monitor the temperature of the second object of interest during medical procedures such as for example during hyperthermia treatment.

Figure 7:
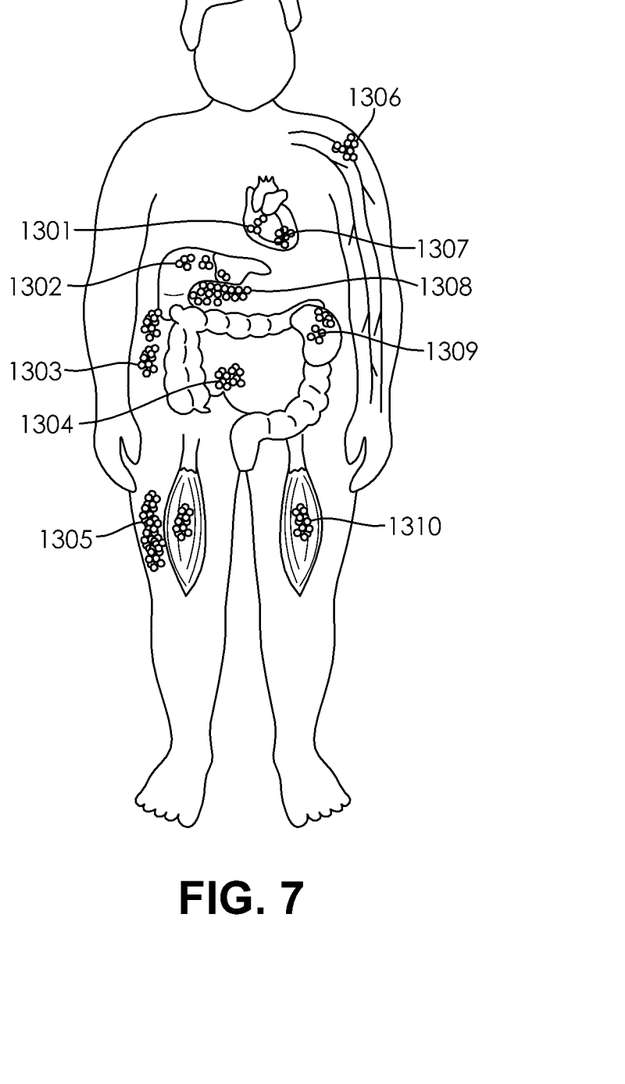
FIG. 7 shows various parts of a human body that can be imaged using the imaging system of FIG. 1.

Although in embodiments the object of interest is described as being the liver and the reference is described as being the kidney, those skilled in the art will appreciate that thermoacoustic data may be obtained for other parts of the body. As shown in FIG. 7, various parts of the body that may be imaged using the above-described system and method include the epi/pericardial adipose tissue 1301, the liver 1302, subcutaneous adipose tissue 1303, visceral adipose tissue 1304, subcutaneous gluteal-femoral adipose tissue 1305, perivascular adipose tissue 1306, myocardial fat 1307, pancreas fat 1308, renal sinus fat 1309, and muscle fat 1310.

It will be appreciated that in some embodiments the thermoacoustic data may be corrected according to a thermoacoustic data adjustment. For example, thermoacoustic signals propagate through space in the form of acoustic pressure waves. Received signals at the ultrasound transducer array can be expressed according to equation 10:

$$p_s(t) = \int_S p(\underline{r},t)dS \quad (10)$$

where S is the surface area of the ultrasound transducer array. Both the properties of the thermoacoustic transducer array and its positioning relative to the region of interest may have an effect on the thermoacoustic data.

Although in embodiments described above the reference is described as being selected by the operator, those skilled in the art will appreciate that alternatives are available. For example, in another embodiment the reference may be automatically defined, using an algorithm performed by the computing device based on known geometry and/or known ultrasound properties of particular types of tissue within the region of interest. Further, the boundary between the reference and the object of interest may be automatically defined using algorithms based on ultrasound segmentation or thermoacoustic data analysis. As will be appreciated, both operator-defined and automatic methods may be combined.

Although in embodiments described above the strength or peak-to-peak amplitude of the bipolar signal is used, those skilled in the art will appreciate that other metrics may be used such as for example a simple peak (maximum), a p-norm, area under the bipolar signal, etc.

As will be appreciated, embodiments described above can be performed in real-time or off-line using images stored in memory.

Although the thermoacoustic imaging system is described as comprising an RF source configured to generate short pulses of RF electromagnetic radiation, those skilled in the art will appreciate that in other embodiments the thermoacoustic imaging system may comprise a visible light source or an infrared radiation source with a wavelengths between 400 nm and 10 μm and a pulse duration between 10 picoseconds and 10 microseconds.

Although in embodiments described above the thermoacoustic imaging system and the ultrasound imaging system are described as using one or more ultrasound transducer arrays, those skilled in the art will appreciate that the alternatives are available. For example, a single transducer element, an ultrasound transducer array having a linear or curved one-dimensional array, or a two-dimensional ultrasound transducer array may be used. In addition, a gel-like material or water capsule may be used to interface the one or more ultrasound transducer arrays with the region of interest.

Although in embodiments described above, the temperature is estimated using thermoacoustic data obtained of a single region of interest, those skilled in the art will appreciate that multiple regions of interest may be analyzed and combined.

Although in embodiments described above blood, vessels are described as being identified manually by an operator, those skilled in the art will appreciate that blood vessels may be identified in other ways. For example, in another embodiment automatic or semi-automatic algorithms may be used to identify one or more blood vessels. In other embodiments, Doppler imaging methods may be used to identify blood vessels.

Those skilled in the art will appreciate that the above-described ultrasound image data and thermoacoustic data may be one-dimensional, two-dimensional or three-dimensional. In embodiments, the ultrasound image data may be in a different dimension than the thermoacoustic data. For example, ultrasound image data may be two-dimensional and the thermoacoustic data may be one-dimensional. Further, different fields of view may be used.

In another embodiment, different types or models of transducer arrays may be used with the thermoacoustic and ultrasound imaging systems. In this embodiment, a transform may be used to map a thermoacoustic absorption image to the ultrasound image. In another embodiment, in the event that knowledge of transducer array geometry is not readily available, the thermoacoustic absorption image may be mapped to the ultrasound image using phantom reference points. In this embodiment, a transform may be used to map known phantom reference points from the thermoacoustic absorption image to the phantom reference points on the ultrasound image.

Although the ultrasound imaging system is described as using B-mode ultrasound imaging techniques, other techniques may be used such as for example power Doppler images, continuous wave Doppler images, etc.

Those skilled in the art will appreciate that other objects of interest may be evaluated and other references may be used such as for example the heart, kidney(s), lung, esophagus, thymus, breast, prostate, brain, muscle, nervous tissue, epithelial tissue, bladder, gallbladder, intestine, liver, pancreas, spleen, stomach, testes, ovaries, uterus, skin and adipose tissues.

Although in embodiments described above thermoacoustic data is obtained, of the region of interest, those skilled in the art will appreciate that thermoacoustic data may be obtained for an area larger than the region of interest.

Using the foregoing specification, the invention may be implemented as a machine, process, or article of manufacture by using standard programming and/or engineering techniques to produce programming software, firmware, hardware or any combination thereof.

Any resulting program(s), having computer-readable instructions, may be stored within one or more computer-usable media such as memory devices or transmitting devices, thereby making a computer program product or article of manufacture according to the invention. As such, functionality may be imparted on a physical device as a computer program existent as instructions on any computer-readable medium such as on any memory device or in any transmitting device, that are to be executed by a processor.

Examples of memory devices include, hard disk drives, diskettes, optical disks, magnetic tape, semiconductor memories such as FLASH, RAM, ROM, PROMS, and the like. Examples of networks include, but are not limited to, the Internet, intranets, telephone/modem-based network communication, hard-wired/cabled communication network, cellular communication, radio wave communication, satellite communication, and other stationary or mobile network systems/communication links.

A machine embodying the invention may involve one or more processing systems including, for example, computer processing unit (CPU) or processor, memory/storage devices, communication links, communication/transmitting devices, servers, I/O devices, or any subcomponents or individual parts of one or more processing systems, including software, firmware, hardware, or any, combination or subcombination thereof, which embody the invention as set forth in the claims.

Using the description provided herein, those skilled in the art will be readily able to combine software created as described with appropriate or special purpose computer hardware to create a computer system and/or computer subcomponents embodying the invention, and to create a computer system and/or computer subcomponents for carrying out the method of the invention.

Although embodiments have been described above with reference to the accompanying drawings, those of skill in the art will appreciate that variations and modifications may be made without departing from the scope thereof as defined by the appended claims.

What is claimed is:

1. A method for estimating tissue temperature, the method comprising:
   (i) directing, using a radio frequency (RF) applicator, one or more RF energy pulses into the tissue region of interest, the tissue region of interest comprising an object of interest and at least one reference that are separated by at least one boundary at least at two boundary locations;
   (ii) detecting, using an acoustic receiver, bipolar acoustic signals generated in the region of interest at each boundary location in response to the one or more RF energy pulses and processing the bipolar acoustic signals to determine peak-to-peak amplitudes thereof; and
   (iii) calculating an estimated tissue temperature at the at least two boundary locations using the peak-to-peak amplitudes of the bipolar acoustic signals and a distance between the boundary locations.

2. The method of claim 1, further comprising calculating the distance between the boundary locations.

3. The method of claim 1, wherein the distance between the boundary locations is an effective distance between the boundary locations.

4. The method of claim 1, further comprising estimating a temperature of the object of interest based on the estimated tissue temperature at the at least two boundary locations.

5. The method of claim 1, further comprising detecting, using the acoustic receiver, at least one other bipolar acoustic signal generated by a second object of interest in response to the one or more RF energy pulses and processing the at least one other bipolar acoustic signal to determine a peak-to-peak amplitude thereof.

6. The method of claim 5, comprising comparing the peak-to-peak amplitude of the bipolar acoustic signal, the calculated temperature at the at least two boundary locations and the peak-to-peak amplitude of the other bipolar acoustic signal to estimate a temperature of the second object of interest.

7. The method of claim 5, wherein the two different types of tissue are one of:
   muscle and fat;
   a blood vessel and fat; and
   liver tissue and kidney tissue.

8. The method of claim 1, wherein each boundary location is between at least two different types of tissue.

9. The method of claim 1, further comprising repeating steps (i) to (iii) during treatment to continuously monitor tissue temperature.

10. A method of monitoring a tissue temperature, the method comprising:
    (i) directing, using a radio frequency (RF) applicator, one or more RF energy pulses into the tissue region of interest, the tissue region of interest comprising an object of interest and at least one reference that are separated by at least one boundary at least at two boundary locations;

(ii) detecting, using an acoustic receiver, bipolar acoustic signals generated in the region of interest at each boundary location in response to the one or more RF energy pulses and processing the bipolar acoustic signals\ to determine peak-to-peak amplitudes thereof;

(iii) calculating an estimated tissue temperature at the at least two boundary locations using the peak-to-peak amplitudes of the bipolar acoustic signals and a distance between the boundary locations; and (iv) repeating the directing, detecting and calculating the estimated tissue temperature to monitor the tissue temperature at the at least one boundary.

11. The method of claim 10, further comprising calculating the distance between the boundary locations.

12. The method of claim 10, wherein the distance between the boundary locations is an effective distance between the boundary locations.

13. The method of claim 10, further comprising:

estimating a temperature of the object of interest based on the estimated tissue temperature at the at least two boundary locations.

14. The method of claim 10, further comprising:

detecting, using the acoustic receiver, at least one other bipolar acoustic signal generated by a second object of interest in response to the one or more RF energy pulses and processing the at least one other bipolar acoustic signal to determine a peak-to-peak amplitude thereof.

15. The method of claim 14, comprising comparing the peak-to-peak amplitude of the bipolar acoustic signal, the calculated temperature at the at least two boundary locations and the peak-to-peak amplitude of the other bipolar acoustic signal to estimate a temperature of the second object of interest.

\* \* \* \* \*